United States Patent
Jenkins et al.

(10) Patent No.: US 9,522,086 B2
(45) Date of Patent: Dec. 20, 2016

(54) HEADBAND FOLDING MECHANISM ALLOWING TWO AXIS FOLDING DIRECTIONS

(71) Applicant: Honeywell International Inc., Morristown, NJ (US)

(72) Inventors: John Jenkins, San Diego, CA (US); Charlotte Loomis, La Jolla, CA (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/590,735

(22) Filed: Jan. 6, 2015

(65) Prior Publication Data

US 2016/0193085 A1   Jul. 7, 2016

(51) Int. Cl.
H04R 25/00   (2006.01)
A61F 11/14   (2006.01)
H04R 1/10    (2006.01)

(52) U.S. Cl.
CPC .............. *A61F 11/14* (2013.01); *H04R 1/1083* (2013.01); *A61F 2250/0075* (2013.01)

(58) Field of Classification Search
CPC ....... H04R 1/1083; H04R 1/1008; H04R 1/10; H04R 1/1016; H04R 1/1058; A61F 11/14; A61F 2250/0075
See application file for complete search history.

(56) References Cited

U.S. PATENT DOCUMENTS

| | | | |
|---|---|---|---|
| 6,385,325 B1 | 5/2002 | Nageno et al. | |
| 6,542,615 B1 | 4/2003 | Ito | |
| 2004/0154082 A1 | 8/2004 | Saffran | |
| 2004/0213428 A1 | 10/2004 | Lenhard-Backhaus | |
| 2004/0216946 A1 | 11/2004 | Lenhard-Backhaus | |
| 2005/0244027 A1* | 11/2005 | Kaulfuss | H04R 5/0335 381/383 |
| 2007/0154051 A1 | 7/2007 | Wang | |
| 2011/0194721 A1* | 8/2011 | Schmidt | H04R 1/1066 381/370 |
| 2012/0140973 A1* | 6/2012 | Olodort | H04R 1/1066 381/375 |

FOREIGN PATENT DOCUMENTS

| | | |
|---|---|---|
| CN | 202497324 U | 10/2012 |
| WO | 2014033472 A3 | 3/2014 |

* cited by examiner

*Primary Examiner* — Tuan D Nguyen
(74) *Attorney, Agent, or Firm* — Conley Rose, P.C.; Kristin Jordan Harkins

(57) ABSTRACT

Embodiments of the disclosure include methods and devices for folding the earmuffs of a headset via at least two different axes of rotation. The headset may comprise a headband and two earmuffs, wherein the earmuffs are connected to the headband, and wherein the headband comprises a plurality of rotational axes, about which the earmuffs may be rotated in one or more directions. The movement of the earmuffs may allow for comfortable wearing of the earmuffs in different positions, such as around a wearer's neck, and may allow for compact carrying or storage of the headset. The headset and earmuffs may be designed to be used as hearing protection, wherein the earmuffs may be larger and comprise special material, and wherein the earmuffs may comply with regulations for hearing protection devices.

18 Claims, 2 Drawing Sheets

HEADBAND FOLDING MECHANISM ALLOWING TWO AXIS FOLDING DIRECTIONS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Hearing protection headsets may comprise large earmuffs attached to a headband to be worn over a wearer's head, holding the earmuffs over the wearer's ears. The earmuffs of a hearing protection headset may comply with hearing protection regulations, wherein the size, shape, and materials may be affected by the regulations. Hearing protection headsets may be worn for extended periods of time while the wearer is working in areas where hearing protection is required.

SUMMARY

Aspects of the disclosure may include embodiments of a method for using a hearing protection headset, wherein the headset comprises a headband and two earmuffs, the method comprising rotating the earmuffs about a first axis and a second axis of the headband from a first position to a second position; wherein rotation of the earmuffs about the first axis and second axis allows inner surfaces of the earmuffs to lay flat against a wearer's chest when the headband is worn around the neck of the wearer, wherein, when the inner surfaces of the earmuffs lay flat against a wearer's chest, the earmuffs are out of the way of movement of the wearer's head and neck.

In some embodiments, the method may further comprise removing the headset from around the neck of the wearer; rotating the earmuffs about the first axis and the second axis from the second position to the first position; and rotating the earmuffs about a third axis and a fourth axis of the headband from the first position to a third position, wherein rotation about the third and fourth axis allows the inner surfaces of the earmuffs to fold toward the headband for compact storage. In some embodiments, rotating the earmuffs about the third axis and the fourth axis may comprise rotating the earmuffs radially with respect to the headband. In some embodiments, rotating the earmuffs about the third axis and the fourth axis may comprise bending the earmuffs about the axes toward the headband. In some embodiments, rotating the earmuffs may further comprise rotating one or more portions of the headband attached to the earmuffs. In some embodiments, rotating the earmuffs about the first axis and the second axis may comprise rotating the earmuffs axially with respect to the headband. In some embodiments, rotating the earmuffs about the first axis and the second axis may comprise spinning or twisting the earmuffs with respect to the headband. In some embodiments, rotating the earmuffs may further comprise rotating one or more portions of the headband attached to the earmuffs. In some embodiments, the method may further comprise moving a microphone attached to the headband out the way of the movement of the wearer's head and neck, wherein the microphone is adjustable with respect to the headband.

Additional aspects of the disclosure may include embodiments of a method for using a hearing protection headset, wherein the headset comprises a headband and two earmuffs, the method comprising wearing the headset for a substantial period of time during a work shift for hearing protection; placing the headset around the neck of a wearer; rotating the earmuffs about a first axis and a second axis of the headband from a first position to a second position, wherein rotation of the earmuffs about the first axis and second axis allows inner surfaces of the earmuffs to lay flat against the wearer's chest when the headband is worn around the neck of the wearer, wherein, when the inner surfaces of the earmuffs lay flat against a wearer's chest, the earmuffs are out of the way of movement of the wearer's head and neck; removing the headset from around the neck of the wearer; rotating the earmuffs about the first axis and the second axis from the second position to the first position; and rotating the earmuffs about a third axis and a fourth axis of the headband from the first position to a third position, wherein rotation about the third and fourth axis allows the inner surfaces of the earmuffs to fold toward the headband for compact storage.

In some embodiments, rotating the earmuffs about the first axis and the second axis may comprise rotating the earmuffs axially with respect to the headband, and rotating the earmuffs about the third axis and the fourth axis may comprise rotating the earmuffs radially with respect to the headband. In some embodiments, rotating the earmuffs from the first position to the second position may further comprise rotating a first earmuff in a first direction, and rotating a second earmuff in a second direction, wherein the first direction and second direction may be similar and symmetrical. In some embodiments, rotating the earmuffs from the first position to the third position may further comprise rotating a first earmuff in a third direction, and rotating a second earmuff in a fourth direction, wherein the third direction and fourth direction may be similar and symmetrical. In some embodiments, rotating the earmuffs may further comprise rotating one or more portions of the headband attached to the earmuffs. In some embodiments, the earmuffs may move independently of one another with respect to the headband.

Other aspects of the disclosure may include embodiments of a hearing protection headset comprising: a headband comprising at least four rotational axes along the length of the headband; two protective earmuffs attached to either end of the headband, wherein the headband holds the earmuffs against the ear of the wearer, wherein rotating a first earmuff about a first axis allows the inner surface of the first earmuff to lay flat against a wearer's chest when the headband is worn around the neck of a wearer; rotating a second earmuff about a second axis allows the inner surface of the second earmuff to lay flat against a wearer's chest when the headband is worn around the neck of a wearer; rotating the first earmuff about a third axis allows the first earmuff to fold toward the headband for compact storage; and rotating the second earmuff about a fourth axis allows the second earmuff to fold toward the headband for compact storage.

In some embodiments, rotation about the first axis may comprise rotating the first earmuff in a first direction, rotation about the second axis may comprise rotating the second earmuff in a second direction, rotation about the third axis may comprise rotating the first earmuff in a third direction, and rotation about the fourth axis may comprise rotating the second earmuff in a fourth direction. In some embodiments, the first direction and second direction may be similar and symmetrical, and the third direction and fourth direction may be similar and symmetrical. In some embodiments, the method may further comprise a microphone attached to the headband, wherein the microphone may be operable to be moved with respect to the headband out the way of the movement of the wearer's head and neck. In some embodiments, the method may further comprise speakers in at least one of the earmuffs, wherein the microphone and speakers may be used for communication purposes.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
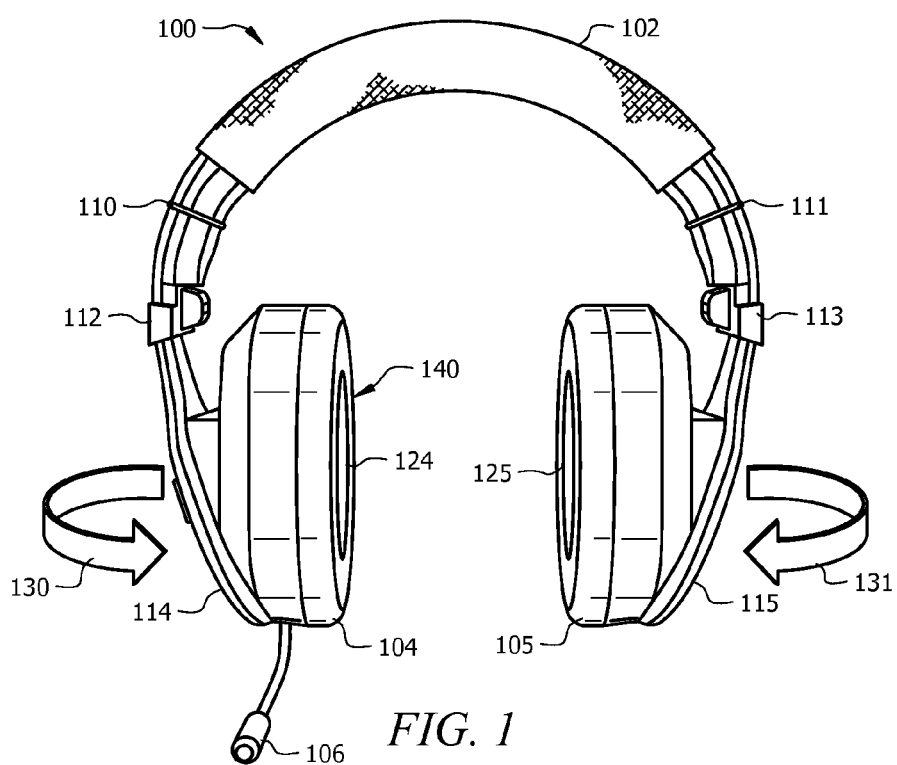
FIG. 1 illustrates an exemplary embodiment of a headset comprising a headband and earmuffs.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include methods and devices for folding the earmuffs of a headset via at least two different axes of rotation. The headset may comprise a headband and two earmuffs, wherein the earmuffs are connected to the headband, and wherein the headband comprises a plurality of rotational axes, about which the earmuffs may be rotated in one or more directions. The movement of the earmuffs may allow for comfortable wearing of the earmuffs in different positions, such as around a wearer's neck, and may allow for compact carrying or storage of the headset. This may be useful for headsets that may be worn for extended periods of time while working, and when a wearer is moving between work areas where hearing protection is needed and work areas when it is not needed.

The headset and earmuffs may be designed to be used as hearing protection, wherein the earmuffs may be larger and comprise special material, and wherein the earmuffs may comply with regulations for hearing protection devices. Additionally, the headset may comprise a microphone and one or more speakers to be used for communication purposes, wherein the speaker(s) may be located within the earmuffs.

Referring now to FIG. 1, an exemplary embodiment of a headset 100 is shown. The headset 100 comprises a headband 102, a first earmuff 104 and a second earmuff 105. The headband 102 may comprise portions 114 and 115 where the earmuffs 104 and 105 attach to the headband 102. In the embodiment of FIG. 1, the headband 102 may comprise a first axis 110 and a third axis 112, about which the first earmuff 104 may rotate. Additionally, the headband 102 may comprise a second axis 111 and a fourth axis 113, about which the second earmuff 105 may rotate. In the embodiment of FIG. 1, the earmuffs 104 and 105 may be in a first position with respect to the headband 102, wherein the first position may be used when the earmuffs 104 and 105 are worn by a wearer.

In some embodiments, the earmuffs 104 and 105 may comprise hearing protection earmuffs, wherein the earmuffs may be designed to be worn for extended periods of time by a wearer while working, for example, in a loud environment where the wearer's hearing may be at risk. Hearing protection earmuffs may comprise specialized sizes, shapes, and materials of construction to provide sufficient protection for the wearer. Hearing protection earmuffs may be designed to follow certain standards or criteria.

In some embodiments, the headset 100 may also comprise a microphone 106 attached to the headband 102 and/or one of the earmuffs 104. In some embodiments, the microphone 106 may be adjustable with respect to the headband 102, wherein a wearer may position the microphone 106 as desired. In some embodiments, the headset 100 may comprise at least one speaker 140 located within at least one of the earmuffs 104, wherein the speaker 140 and the microphone 106 may be used for communication purposes.

Figure 2:
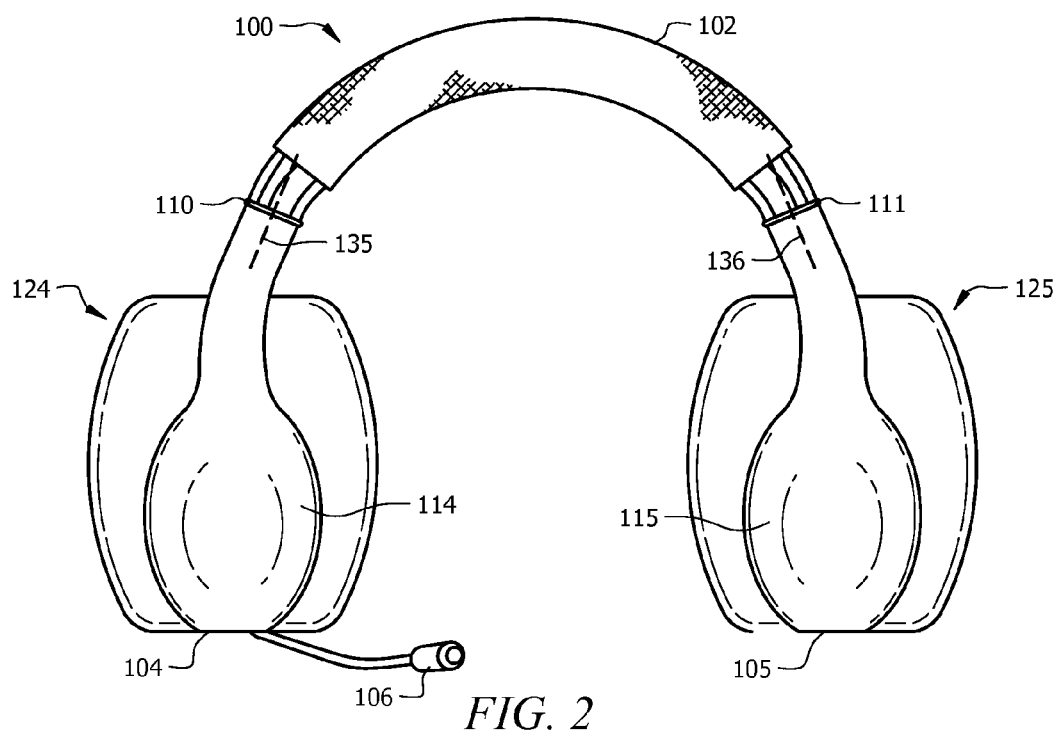
FIG. 2 illustrates an exemplary embodiment of a folding method for a headset.

In the embodiment shown in FIG. 1, the earmuffs 104 and 105 may be operable to rotate about the first axis 110 and second axis 111 in a first direction 130 and second direction 131. As shown in FIG. 2, the earmuffs 104 and 105 may rotate in the first direction 130 and second direction 131 about the first and second axes 110 and 111. In some embodiments, the movement of the earmuff 104 with respect to the headband 102 may comprise the portion 114 of the headband 102 that attaches to the earmuff 104 rotating axially with respect to the headband 102. In other words, the first axis 110 may allow the portion 114 of the headband 102 to twist or spin about a central axis 135 with respect to the headband 102. Additionally, the earmuff 105, headband 102, and the portion 115 of the headband 102 attached to the earmuff 105 may move in a similar fashion at the second axis 111 about a central axis 136, wherein the movement of the earmuff 105 may be symmetrical to the movement of the earmuff 104. In some embodiments, the movement of each of the earmuffs 104 and 105 may be independent from one another, wherein one earmuff may move without the other earmuff moving.

In the embodiment of FIG. 2, the earmuffs 104 and 105 may be in a second position. In some embodiments, the wearer may wear the headband 102 around their neck, for example when the earmuff 104 and 105 are not required for wearing, but the wearer wishes to keep the headset 100 accessible. By rotating about the first and second axes 110 and 111, an inner surface 124 of the first earmuff 104 and an inner surface 125 of the second earmuff 105 may be turned toward the chest of the wearer (when the headband 102 is around the neck of the wearer). The inner surfaces 124 and 125 of the earmuffs 104 and 105 may lay flat against the chest of the wearer, allowing for unimpeded movement of the wearer's head and neck when the headset 100 is worn around the wearer's neck. In some embodiments, the microphone 106 may also lay flat and/or may be positioned toward the wearer's chest, moving the microphone 106 out of the way of the movement of the wearer's head and neck.

Figure 3:
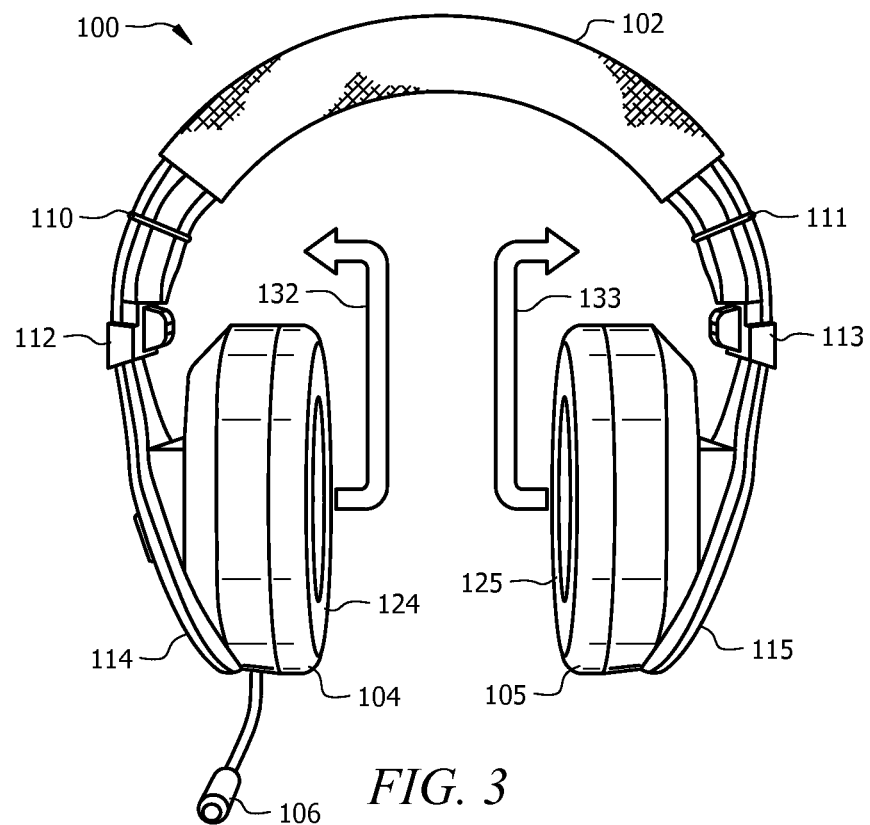
FIG. 3 illustrates another exemplary embodiment of a folding method for a headset.

FIG. 3 illustrates another exemplary embodiment of the headset 100, wherein the earmuffs 104 and 105 may be operable to move in a third direction 132 and fourth direction 133 toward the headband 102. In FIG. 3 the earmuffs 104 and 105 may be in the first position (similar to FIG. 1). In the embodiment of FIG. 3, the earmuffs 104 and 105 may rotate about the third axis 112 and fourth axis 113. Movement in the third and fourth directions 132 and 133 may allow the earmuffs 104 and 105 to move to a more compact third position, for example, for storage of the headset 100.

Figure 4:
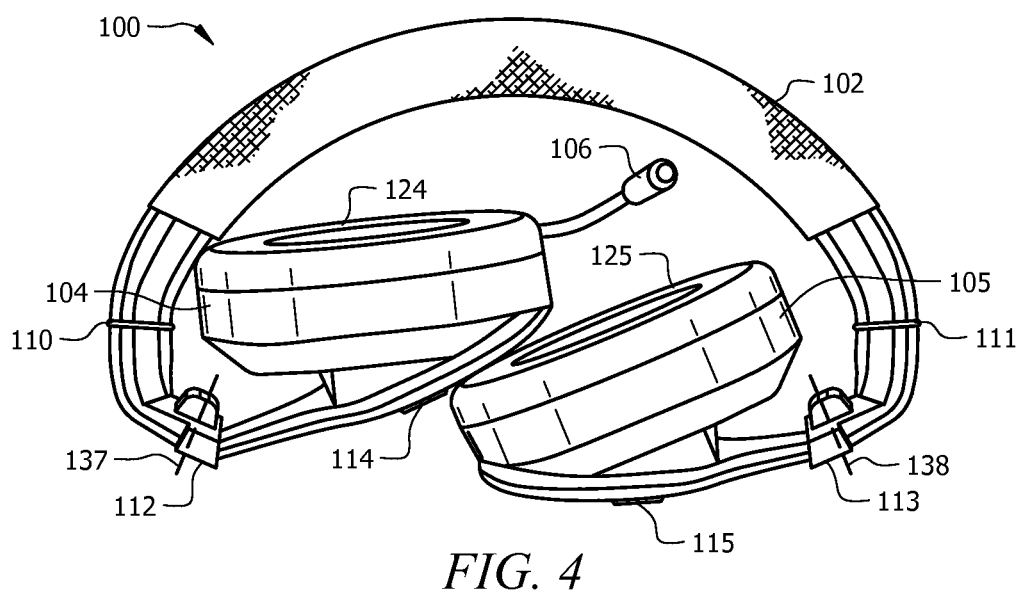
FIG. 4 illustrates yet another exemplary embodiment of a folding method for a headset.

FIG. 4 illustrates the third position of the earmuffs 104 and 105 with respect to the headband, wherein the third position may be used for storage or carrying of the headset 100 when it is not being worn by a wearer. The earmuffs 104 and 105 may move toward each other and toward the headband 102 to reduce the size of the headset 100. In some embodiments, the microphone 106 may also be operable to move toward the earmuff 104 and/or headband 102, making the headset 100 more compact and easier to carry or store.

In some embodiments, the movement of the earmuff 104 with respect to the headband 102 may comprise the portion 114 of the headband 102 that attaches to the earmuff 104 rotating radially with respect to the headband 102. In other words, the third axis 112 may allow the portion 114 of the headband 102 to bend or swing about a central axis 137 with respect to the headband 102. Additionally, the earmuff 105, headband 102, and the portion 115 of the headband 102 attached to the earmuff 105 may move in a similar fashion at the second axis 111 about a central axis 138, wherein the movement of the earmuff 105 may be symmetrical to the movement of the earmuff 104. In some embodiments, the movement of each of the earmuffs 104 and 105 may be independent from one another, wherein one earmuff may move without the other earmuff moving. For example, in the embodiment of FIG. 4, the first earmuff 104 may be moved toward the headband 102 first, while the second earmuff 105 is moved toward the headband 102 second and moved on top of the first earmuff 104.

Embodiments of the disclosure may include one or more method for using a hearing protection headset. The method may comprise rotating the earmuffs about a first axis and a second axis of the headband from a first position to a second position, wherein rotation of the earmuffs about the first axis and second axis allows inner surfaces of the earmuffs to lay flat against a wearer's chest when the headband is worn around the neck of the wearer, wherein, when the inner surfaces of the earmuffs lay flat against a wearer's chest, the earmuffs are out of the way of movement of the wearer's head and neck. In other embodiments, the method may also comprise wearing the headset for a substantial period of time during a work shift for hearing protection, and placing the headset around the neck of a wearer.

In some embodiments, the method may further comprise removing the headset from around the neck of the wearer, rotating the earmuffs about the first axis and the second axis from the second position to the first position, and rotating the earmuffs about a third axis and a fourth axis of the headband from the first position to a third position, wherein rotation about the third and fourth axis allows the inner surfaces of the earmuffs to fold toward the headband for compact storage. In some embodiments, the method may further comprise moving a microphone attached to the headband out the way of the movement of the wearer's head and neck, wherein the microphone is adjustable with respect to the headband.

In some embodiments, rotating the earmuffs about the third axis and the fourth axis may comprise rotating the earmuffs radially with respect to the headband. In some embodiments, rotating the earmuffs about the third axis and the fourth axis may comprise bending the earmuffs about the axes toward the headband. In some embodiments, rotating the earmuffs may further comprise rotating one or more portions of the headband attached to the earmuffs. In some embodiments, rotating the earmuffs about the first axis and the second axis may comprise rotating the earmuffs axially with respect to the headband. In some embodiments, rotating the earmuffs about the first axis and the second axis may comprise spinning or twisting the earmuffs with respect to the headband. In some embodiments, rotating the earmuffs further comprises rotating one or more portions of the headband attached to the earmuffs.

In some embodiments, rotating the earmuffs from the first position to the second position may further comprise rotating a first earmuff in a first direction, and rotating a second earmuff in a second direction, wherein the first direction and second direction are similar and symmetrical. In some embodiments, rotating the earmuffs from the first position to the third position may further comprise rotating a first earmuff in a third direction, and rotating as second earmuff in a fourth direction, wherein the third direction and fourth direction are similar and symmetrical. In some embodiments, the earmuffs may move independently of one another with respect to the headband.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower tennis such as consisting of, consisting essentially of, and comprised substantially of use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method for using a hearing protection headset, wherein the headset comprises a headband and two earmuffs, the headband comprising:
   a first axis configured to allow a first terminal portion of the headband having a first of the two earmuffs attached thereto to rotate axially with respect to a central portion of the headband; and
   a second axis configured to allow a second terminal portion of the headband having a second of the two earmuffs attached thereto to rotate axially with respect to the central portion of the headband, the method comprising:
   axially rotating the earmuffs about the first axis and the second axis of the headband from a first position to a second position, wherein axial rotation of the earmuffs about the first axis and second axis allows inner surfaces of the earmuffs to lay flat against a wearer's chest when the headband is worn around the neck of the wearer, wherein, when the inner surfaces of the earmuffs lay flat against a wearer's chest, the earmuffs are out of the way of movement of the wearer's head and neck.

2. The method of claim 1, further comprising:
   removing the headset from around the neck of the wearer;
   axially rotating the earmuffs about the first axis and the second axis from the second position to the first position; and
   rotating the earmuffs about a third axis and a fourth axis of the headband from the first position to a third position, wherein rotation about the third and fourth axis allows the inner surfaces of the earmuffs to fold toward the headband for compact storage.

3. The method of claim 2, wherein rotating the earmuffs about the third axis and the fourth axis comprises rotating the earmuffs radially with respect to the headband.

4. The method of claim 2, wherein rotating the earmuffs about the third axis and the fourth axis comprises bending the earmuffs about the axes toward the headband.

5. The method of claim 2, wherein rotating the earmuffs further comprises rotating one or more portions of the headband attached to the earmuffs.

6. The method of claim 1, wherein axially rotating the earmuffs about the first axis and the second axis comprises axially rotating the earmuffs axially with respect to the headband.

7. The method of claim 1, wherein axially rotating the earmuffs about the first axis and the second axis comprises spinning or twisting the earmuffs with respect to the headband.

8. The method of claim 1 further comprising moving a microphone attached to the headband out the way of the movement of the wearer's head and neck, wherein the microphone is adjustable with respect to the headband.

9. A method for using a hearing protection headset, wherein the headset comprises a headband and two earmuffs, the headband comprising:
   a first axis configured to allow a first terminal portion of the headband having a first of the two earmuffs attached thereto to rotate axially with respect to a central portion of the headband; and
   a second axis configured to allow a second terminal portion of the headband having a second of the two earmuffs attached thereto to rotate axially with respect to the central portion of the headband, the method comprising:

wearing the headset for a substantial period of time during a work shift for hearing protection;

placing the headset around the neck of a wearer;

axially rotating the earmuffs about the first axis and the second axis of the headband from a first position to a second position, wherein axial rotation of the earmuffs about the first axis and second axis allows inner surfaces of the earmuffs to lay flat against the wearer's chest when the headband is worn around the neck of the wearer, wherein, when the inner surfaces of the earmuffs lay flat against a wearer's chest, the earmuffs are out of the way of movement of the wearer's head and neck;

removing the headset from around the neck of the wearer;

axially rotating the earmuffs about the first axis and the second axis from the second position to the first position; and rotating the earmuffs about a third axis and a fourth axis of the headband from the first position to a third position, wherein rotation about the third and fourth axis allows the inner surfaces of the earmuffs to fold toward the headband for compact storage.

10. The method of claim 9, wherein rotating the earmuffs about the third axis and the fourth axis comprises rotating the earmuffs radially with respect to the headband.

11. The method of claim 9, wherein rotating the earmuffs from the first position to the second position further comprises:

axially rotating a first earmuff in a first direction; and axially rotating a second earmuff in a second direction, wherein the first direction and second direction are similar and symmetrical.

12. The method of claim 9, wherein axially rotating the earmuffs from the first position to the third position further comprises:

rotating a first earmuff in a third direction; and rotating a second earmuff in a fourth direction, wherein the third direction and fourth direction are similar and symmetrical.

13. The method of claim 9, wherein the earmuffs move independently of one another with respect to the headband.

14. A hearing protection headset comprising:

a headband comprising at least four rotational axes along the length of the headband, the four rotational axes including:

a first axis configured to allow a first terminal portion of the headband having a first of the two earmuffs attached thereto to rotate axially with respect to a central portion of the headband; and a second axis configured to allow a second terminal portion of the headband having a second of the two earmuffs attached thereto to rotate axially with respect to the central portion of the headband; and two protective earmuffs attached to either end of the headband, wherein the headband holds the earmuffs against the ear of a wearer, wherein:

axially rotating a first earmuff about the first axis allows an inner surface of the first earmuff to lay flat against a wearer's chest when the headband is worn around the neck of a wearer;

axially rotating a second earmuff about the second axis allows an inner surface of the second earmuff to lay flat against a wearer's chest when the headband is worn around the neck of a wearer;

rotating the first earmuff about a third axis allows the first earmuff to fold toward the headband for compact storage; and rotating the second earmuff about a fourth axis allows the second earmuff to fold toward the headband for compact storage.

15. The headset of claim 14, wherein axial rotation about the first axis comprises axially rotating the first earmuff in a first direction, wherein axial rotation about the second axis comprises rotating the second earmuff in a second direction, wherein rotation about the third axis comprises rotating the first earmuff in a third direction, and wherein rotation about the fourth axis comprises rotating the second earmuff in a fourth direction.

16. The headset of claim 15, wherein the first direction and second direction are similar and symmetrical, and wherein the third direction and fourth direction are similar and symmetrical.

17. The headset of claim 14 further comprising a microphone attached to the headband, wherein the microphone is operable to be moved with respect to the headband out the way of the movement of the wearer's head and neck.

18. The headset of claim 17 further comprising speakers in at least one of the earmuffs, wherein the microphone and speakers are used for communication purposes.

* * * * *

UNITED STATES PATENT AND TRADEMARK OFFICE
CERTIFICATE OF CORRECTION

| | | |
|---|---|---|
| PATENT NO. | : 9,522,086 B2 | Page 1 of 1 |
| APPLICATION NO. | : 14/590735 | |
| DATED | : December 20, 2016 | |
| INVENTOR(S) | : John Jenkins and Charlotte Loomis | |

It is certified that error appears in the above-identified patent and that said Letters Patent is hereby corrected as shown below:

In the Specification

Column 4, Line 30: "104 and" should be "104, and"

Column 5, Line 34: "FIG. 3 the" should be "FIG. 3, the"

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*